(12) United States Patent
Tate

(10) Patent No.: US 11,378,561 B2
(45) Date of Patent: Jul. 5, 2022

(54) AUTOMATED SPECTRAL LIBRARY RETENTION TIME CORRECTION

(71) Applicant: DH TECHNOLOGIES DEVELOPMENT PTE. LTD., Singapore (SG)

(72) Inventor: Stephen A. Tate, Barrie (CA)

(73) Assignee: DH Technologies Development Pte. Ltd., Singapore (SG)

( * ) Notice: Subject to any disclaimer, the term of this patent is extended or adjusted under 35 U.S.C. 154(b) by 816 days.

(21) Appl. No.: 16/323,489

(22) PCT Filed: Jul. 19, 2017

(86) PCT No.: PCT/IB2017/054384
§ 371 (c)(1),
(2) Date: Feb. 5, 2019

(87) PCT Pub. No.: WO2018/029554
PCT Pub. Date: Feb. 15, 2018

(65) Prior Publication Data
US 2021/0293764 A1 Sep. 23, 2021

Related U.S. Application Data

(60) Provisional application No. 62/372,854, filed on Aug. 10, 2016.

(51) Int. Cl.
*G01N 30/72* (2006.01)
*G01N 30/86* (2006.01)
(Continued)

(52) U.S. Cl.
CPC ......... *G01N 30/8682* (2013.01); *G01N 30/72* (2013.01); *G16C 20/20* (2019.02);
(Continued)

(58) Field of Classification Search
CPC ............... G01N 30/8682; G01N 30/72; G01N 30/8668; G16C 20/20; G16C 20/70; H01J 49/0036; H01J 49/004
(Continued)

(56) References Cited

U.S. PATENT DOCUMENTS

2014/0297201 A1* 10/2014 Knorr ................ G01N 30/8693
702/28
2014/0332681 A1 11/2014 Tate et al.
(Continued)

FOREIGN PATENT DOCUMENTS

WO 2016046513 A1 3/2016

OTHER PUBLICATIONS

International Search Report and Written Opinion for PCT/IB2017/054384, dated Nov. 9, 2017.

*Primary Examiner* — Michael Maskell
(74) *Attorney, Agent, or Firm* — Kasha Law LLC; John R. Kasha; Kelly L. Kasha

(57) ABSTRACT

A plurality of measured product ion spectra is produced using a DIA tandem mass spectrometry method. One or more product ions are retrieved from a spectral library of known compounds or one or more theoretical product ions are calculated for the known compounds of a database. For each known or theoretical product ion, an XIC is calculated from the measured product ion spectra. Measured XIC peaks above a threshold intensity are grouped for the known compounds producing a subset of known compounds. Known or theoretical retention times are retrieved or calculated for the subset of known compounds. A regression function is calculated to correct the known or theoretical retention times using the known or theoretical retention times of the subset of known compounds as the independent variables and the measured retention times of the measured (Continued)

XIC peak groups of the subset of known compounds as the dependent variables.

14 Claims, 8 Drawing Sheets

(51) Int. Cl.
    *G16C 20/20*     (2019.01)
    *G16C 20/70*     (2019.01)
    *H01J 49/00*     (2006.01)

(52) U.S. Cl.
    CPC ............ *G16C 20/70* (2019.02); *H01J 49/004* (2013.01); *H01J 49/0036* (2013.01)

(58) Field of Classification Search
    USPC .............................. 702/27, 28; 250/281, 282
    See application file for complete search history.

(56) References Cited

U.S. PATENT DOCUMENTS

2015/0162175 A1     6/2015   Wright
2016/0025691 A1     1/2016   Taneda

\* cited by examiner

AUTOMATED SPECTRAL LIBRARY RETENTION TIME CORRECTION

CROSS REFERENCE TO RELATED APPLICATION

This application claims the benefit of U.S. Provisional Patent Application Ser. No. 62/372,854, filed Aug. 10, 2016, the content of which is incorporated by reference herein in its entirety.

INTRODUCTION

The teachings herein relate to the identification of known compounds in a sample mixture using a separation technique coupled to tandem mass spectrometry or mass spectrometry/mass spectrometry (MS/MS). More particularly the teachings herein relate to systems and methods for correcting retention times of theoretical ions or stored library ions on a per sample basis so that they can be compared to the measured retention times of ions of a sample mixture and used in the identification of known compounds in a sample mixture.

BACKGROUND

A common problem in mass spectrometry is determining the identity of compounds present in a sample. In proteomics, for example, the problem is determining the identity of proteins present in the sample. Typically, compounds or proteins are identified in a sample using a two-step tandem mass spectrometry process.

In the first step, experimental data is obtained. The proteins in a sample are digested using an enzyme such as trypsin, producing one or more peptides for each protein. Note that a peptide, as used herein, is a digested portion of a protein. Some proteins can be digested intact, so a peptide can also be the entire protein. However, in most cases, peptides are digested portions of proteins.

The peptides digested from proteins are then separated from the sample over time using a sample introduction device or separation device. The separated peptides are then ionized using an ion source. The ionized peptides, or peptide precursor ions, are selected by mass-to-charge ratio (m/z), the selected precursor ions are fragmented, and the resulting product ions are mass analyzed using a tandem mass spectrometer. The result of the first step is a collection of one or more product ion mass spectra measured at one or more different times.

In the second step, information about known compounds or proteins expected to be in the experimental sample is obtained from stored spectral library or database or is computer generated. This known data is compared to the experimental data. This known data includes, for example, mass-to-charge ratio values of product ions at specific retention times.

Information about product ions of known compounds, for example, can be obtained from a spectral library or database. A spectral library includes, for example, spectral data collected from analyzing each of the known compounds separately. Product ions from this previously collected spectral data are then compared to each of the one or more measured product ion mass spectra measured from a sample mixture at each of the one or more different times. Typically, known compounds are scored based on how well their library product ions match the one or more measured product ion mass spectra. The compounds in the sample mixture are then identified from the highest scoring known compounds.

Similarly, known proteins, for example, can be obtained from a database, and can be computationally digested using the same enzyme used in the tandem mass spectrometry experiment, producing one or more theoretical peptides for each known protein. Theoretical peptides are computationally selected and fragmented, producing theoretical product ions for each known protein. Theoretical retention times can also be calculated. The resulting theoretical product ions are then compared to each of the one or more measured product ion mass spectra at each of the one or more different times. Typically, known proteins are scored based on how well their theoretical product ions match the one or more measured product ion mass spectra. The proteins in the sample are then identified from the highest scoring known proteins.

As a result, known compounds or proteins in a sample mixture can be identified by comparing library or theoretical product ion m/z and retention time values to experimental product ion m/z and retention time values measured from the sample mixture.

Unfortunately, however, library or theoretical retention time values often do not quite match the measured retention time values. This is due to the fact that the separation media used in measuring the library retention time values or used in calculating the theoretical retention time values is not the same as the separation media used to measure the sample mixture. This inaccuracy in the library or theoretical retention time values can adversely affect the identification of compounds or proteins.

One method of addressing this problem has been to develop internal retention time standards. Another method that has been proposed is to use markers, landmark peptides, or housekeeping proteins. There are few commercial kits available for this purpose. A problem with both of these methods is that they do not provide enough information to accurately correct for the thousands of different compounds or peptides that may be present in a sample mixture. In other words, these methods limit the number of compounds that can be analyzed at any one time.

Still another method of addressing this problem has been to use computer generated retention times. An exemplary open source retention time calculator is SSRcalc. This approach allows retention times to be calculated for a large number of compounds. However, this approach has little relationship to the sample mixture or the separation media used.

Consequently, systems and methods are needed to accurately correct the retention times of spectral libraries or theoretical product ions based on a specific sample mixture and experiment so that they can be compared to the retention times measured in the experiment and used to identify known compounds.

Accurately correcting the retention times of spectral libraries or theoretical product ions is particularly important for data independent acquisition (DIA) methods. DIA is a tandem mass spectrometry workflow. In general, tandem mass spectrometry, or MS/MS, is a well-known technique for analyzing compounds. Tandem mass spectrometry involves ionization of one or more compounds from a sample, selection of one or more precursor ions of the one or more compounds, fragmentation of the one or more precursor ions into product ions, and mass analysis of the product ions.

Tandem mass spectrometry can provide both qualitative and quantitative information. The product ion spectrum can be used to identify a molecule of interest. The intensity of one or more product ions can be used to quantitate the amount of the compound present in a sample.

A large number of different types of experimental methods or workflows can be performed using a tandem mass spectrometer. Three broad categories of these workflows are, targeted acquisition, information dependent acquisition (IDA) or data dependent acquisition (DDA), and DIA.

In a targeted acquisition method, one or more transitions of a peptide precursor ion to a product ion are predefined for one or more proteins. As a sample is being introduced into the tandem mass spectrometer, the one or more transitions are interrogated during each time period or cycle of a plurality of time periods or cycles. In other words, the mass spectrometer selects and fragments the peptide precursor ion of each transition and performs a targeted mass analysis for the product ion of the transition. As a result, a mass spectrum is produced for each transition. Targeted acquisition methods include, but are not limited to, multiple reaction monitoring (MRM) and selected reaction monitoring (SRM).

IDA is a flexible tandem mass spectrometry method in which a user can specify criteria for performing targeted or untargeted mass analysis of product ions while a sample is being introduced into the tandem mass spectrometer. For example, in an IDA method a precursor ion or mass spectrometry (MS) survey scan is performed to generate a precursor ion peak list. The user can select criteria to filter the peak list for a subset of the precursor ions on the peak list. MS/MS is then performed on each precursor ion of the subset of precursor ions. A product ion spectrum is produced for each precursor ion. MS/MS is repeatedly performed on the precursor ions of the subset of precursor ions as the sample is being introduced into the tandem mass spectrometer.

In proteomics and many other sample types, however, the complexity and dynamic range of compounds are very large. This poses challenges for traditional targeted and IDA methods, requiring very high-speed MS/MS acquisition to deeply interrogate the sample in order to both identify and quantify a broad range of analytes.

As a result, DIA methods have been used to increase the reproducibility and comprehensiveness of data collection from complex samples. DIA methods can also be called non-specific fragmentation methods. In a traditional DIA method, the actions of the tandem mass spectrometer are not varied among MS/MS scans based on data acquired in a previous precursor or product ion scan. Instead, a precursor ion mass range is selected. A precursor ion mass selection window is then stepped across the precursor ion mass range. All precursor ions in the precursor ion mass selection window are fragmented and all of the product ions of all of the precursor ions in the precursor ion mass selection window are mass analyzed.

The precursor ion mass selection window used to scan the mass range can be very narrow so that the likelihood of multiple precursors within the window is small. This type of DIA method is called, for example, MS/MS$^{ALL}$. In an MS/MS$^{ALL}$ method, a precursor ion mass selection window of about 1 amu is scanned or stepped across an entire mass range. A product ion spectrum is produced for each 1 amu precursor mass window. A product ion spectrum for the entire precursor ion mass range is produced by combining the product ion spectra for each mass selection window. The time it takes to analyze or scan the entire mass range once is referred to as one scan cycle. Scanning a narrow precursor ion mass selection window across a wide precursor ion mass range during each cycle, however, is not practical for some instruments and experiments.

As a result, a larger precursor ion mass selection window, or selection window with a greater width, is stepped across the entire precursor mass range. This type of DIA method is called, for example, SWATH acquisition. In SWATH acquisition the precursor ion mass selection window stepped across the precursor mass range in each cycle may have a width of 5-25 amu, or even larger. Like the MS/MS$^{ALL}$ method, all the precursor ions in each precursor ion mass selection window are fragmented, and all of the product ions of all of the precursor ions in each mass isolation window are mass analyzed. However, because a wider precursor ion mass selection window is used, the cycle time can be significantly reduced in comparison to the cycle time of the MS/MS$^{ALL}$ method.

U.S. Pat. No. 8,809,770 describes how SWATH acquisition can be used to provide quantitative and qualitative information about the precursor ions of compounds of interest. In particular, the product ions found from fragmenting a precursor ion mass selection window are compared to a database of known product ions of compounds of interest. In addition, ion traces or extracted ion chromatograms (XICs) of the product ions found from fragmenting a precursor ion mass selection window are analyzed to provide quantitative and qualitative information.

As described above, however, identifying proteins in a sample analyzed using SWATH acquisition, for example, can be difficult, because there is no peptide precursor ion information provided with a precursor ion mass selection window to help determine the precursor ion that produces each product ion. In addition, because there is no peptide precursor ion information provided with a precursor ion mass selection window, it is also difficult to determine if a product ion is convolved with or includes contributions from multiple precursor ions within the precursor ion mass selection window.

Retention time can be used in DIA methods and in SWATH acquisition in particular to both determine the precursor ion that produces each product ion and determine if a product ion is convolved with or includes contributions from multiple precursor ions. As a result, determining an accurate retention time for a known compound or protein in a DIA method is particularly important.

Conventionally, DIA methods include a manual alignment step to correct retention times for a sample mixture. In this step, for each sample, a user selects a small number of known compounds to align the retention times against. During the experiment, the actual and experimental retention time differences of the selected known compounds are measured, and these differences are used to correct the retention times of all the known compounds used in the experiment. Like the methods mentioned above regarding internal standards and experimental markers, this method does not provide enough information to accurately correct for the thousands of different compounds or peptides that may be present in a sample mixture. As a result, in particular, systems and methods are needed to accurately and automatically correct the retention times of spectral libraries or theoretical product ions in a DIA experiment based on a specific sample mixture and experiment so that they can be compared to the retention times measured in the experiment and used to identify known compounds.

SUMMARY

A system is disclosed for automatically calculating a regression function to describe how the known retention times of a spectral library of known compounds are varied by the sample in a tandem mass spectrometry data independent acquisition (DIA) experiment. A similar system is disclosed for automatically calculating a regression function to describe how the theoretical retention times of the theoretical product ions of known compounds are varied by the sample in a tandem mass spectrometry DIA experiment.

Both systems include a separation device, an ion source, a tandem mass spectrometer, and a processor. The separation device separates compounds from a sample over time. The ion source receives the plurality of compounds from the separation device and ionizes the plurality of compounds, producing an ion beam of precursor ions. The tandem mass spectrometer receives the ion beam from the ion source, divides an m/z range of the ion beam into two or more precursor ion mass selection windows, and selects and fragments the two or more precursor ion mass selection windows during each cycle of a plurality of cycles, producing a plurality of measured product ion spectra.

The processor receives the plurality of measured product ion spectra from the tandem mass spectrometer. In one system, the processor retrieves from a spectral library of known compounds one or more product ions for each known compound. In the other system, the processor retrieves a plurality of known compounds from a database. For each known compound of the database, the processor theoretically fragments the known compound, producing one or more theoretical product ions.

For each product ion of each known compound of the spectral library or the database, the processor calculates an XIC from the plurality of measured product ion spectra. The processor groups XIC peaks with an intensity above a predetermined intensity threshold value from the XICs calculated for each known compound of the spectral library by the measured retention time. One or more measured XIC peak groups are produced for a subset of known compounds of the spectral library that have measured XIC peaks with an intensity above the predetermined intensity threshold value.

In one system, the processor retrieves from the spectral library a known retention time for each known compound of the subset of known compounds. In the other system, for known compounds obtained from a database, the processor calculates a theoretical retention time for each known compound of the subset of known compounds.

Finally, the processor calculates a regression function to describe how the known retention times of the spectral library or the theoretical retention times calculated for the known compound database are varied in the sample. The regression function is calculated using the known or theoretical retention times of the subset of known compounds as the independent variables. The measured retention times of the measured XIC peak groups of the subset of known compounds are used as the dependent variables.

Similarly, a method is disclosed for automatically calculating a regression function to describe how the known retention times of a spectral library of known compounds are varied by the sample in a tandem mass spectrometry DIA experiment, in accordance with various embodiments. Another method is disclosed for automatically calculating a regression function to describe how the theoretical retention times of the theoretical product ions of known compounds are varied by the sample in a tandem mass spectrometry DIA experiment.

In both methods, a plurality of measured product ion spectra are received from a tandem mass spectrometer.

In one method, one or more product ions for each known compound are retrieved from a spectral library of known compounds. In the other method, a plurality of known compounds is retrieved from a database. For each known compound of the plurality of known compounds, the known compound is theoretically fragmented producing one or more theoretical product ions.

For each product ion of each known compound of the spectral library or the database, an XIC is calculated from the plurality of measured product ion spectra. XIC peaks with an intensity above a predetermined intensity threshold value from the XICs calculated for each known compound of the spectral library or the database are grouped by the measured retention time, producing one or more measured XIC peak groups for a subset of known compounds of the spectral library or the library that have measured XIC peaks with an intensity above the predetermined intensity threshold value.

In one method, a known retention time for each known compound of the subset of known compounds is retrieved from the spectral library. In the other method, a theoretical retention time is calculated for each known compound of the subset of known compounds.

Finally, a regression function is calculated to describe how the known retention times of the spectral library or the theoretical retention times of the database are varied in the sample. The known or theoretical retention times of the subset of known compounds are used as the independent variables. The measured retention times of the measured XIC peak groups of the subset of known compounds are used as the dependent variables.

These and other features of the applicant's teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

Figure 1:
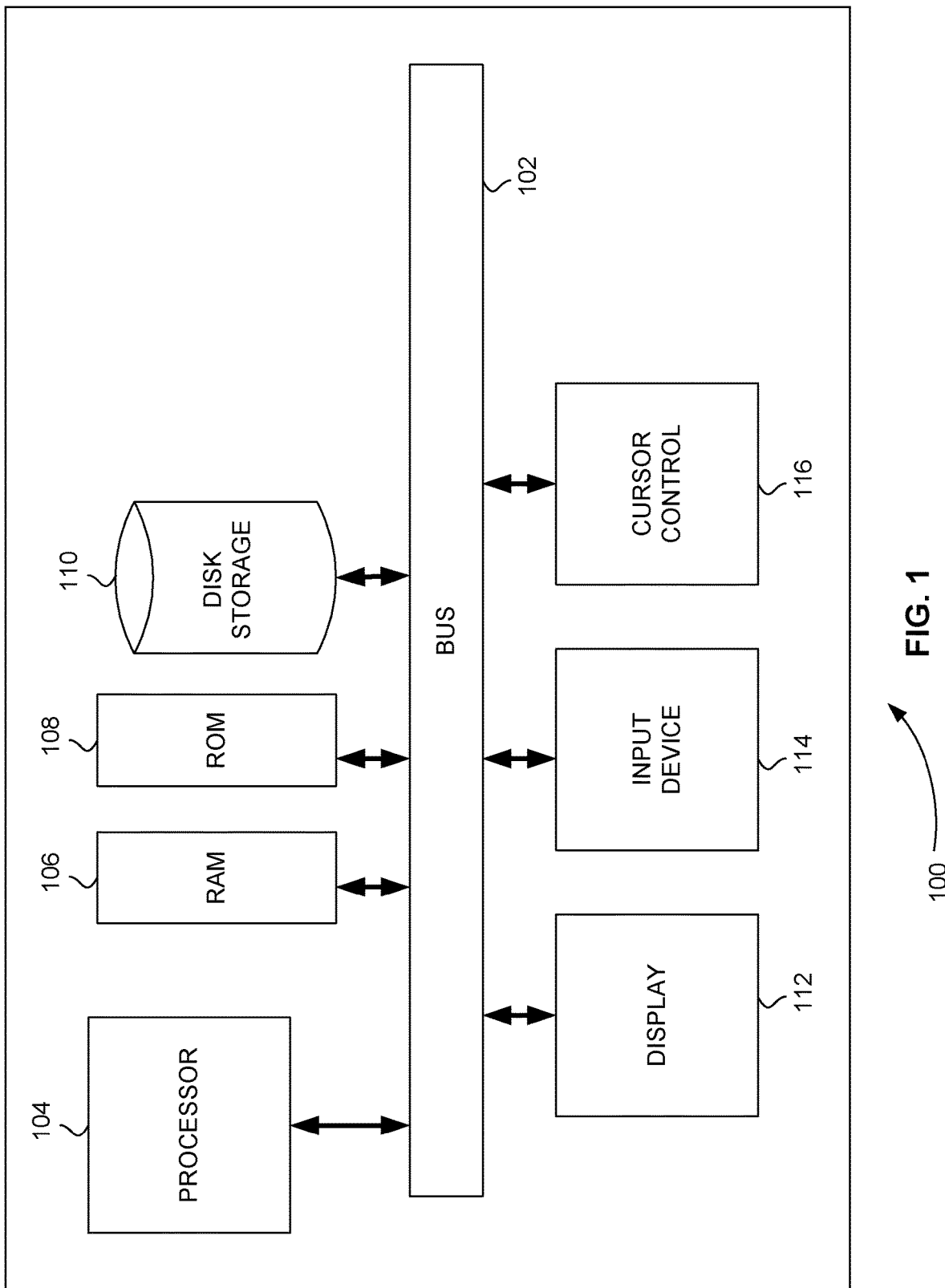
FIG. 1 is a block diagram that illustrates a computer system, upon which embodiments of the present teachings may be implemented.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively, hard-wired circuitry may be used in place of or in combination with software instructions to implement the present teachings. Thus implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system, one or more computer systems can store and serve the data to other computer systems. The one or more computer systems that store and serve the data can be referred to as servers or the cloud, in a cloud computing scenario. The one or more computer systems can include one or more web servers, for example. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Regression Analysis to Determine Retention Time As described above, data independent acquisition (DIA) methods generally include a manual alignment step to correct retention times for a sample mixture. In this step, for each sample, a user selects a small number of known compounds to align the retention times against. During the experiment, the actual and experimental retention time differences of the selected known compounds are measured, and these differences are used to correct the retention times of all the known compounds used in the experiment. Like the methods mentioned above regarding internal standards and experimental markers, this method does not provide enough information to accurately correct for the thousands of different compounds or peptides that may be present in a sample mixture. As a result, systems and methods are needed to accurately and automatically correct the retention times of spectral libraries or theoretical product ions in a DIA experiment based on a specific sample mixture and experiment so that they can be compared to the retention times measured in the experiment and used to identify known compounds.

In various embodiments, regression analysis is used to automatically correct the retention times of a spectral library or the theoretical retention times of theoretical product ions for a particular sample. Specifically, after a DIA experiment, all of the measured product ion data for all of the product ions of a spectral library or for all of the theoretical product ions generated for a known compound database are extracted. In this first pass through the data, the measured product ion data is extracted without regard to retention time. The extracted measured product ion data includes an extracted ion chromatogram (XIC) for each product ion of a spectral library or each theoretical product ion generated for a known compound database.

XIC peaks above a predetermined intensity threshold are found in the extracted XICs. The XIC peaks found are then grouped by their measured retention times. The number of known compounds from the spectral library or known compound database found to have one or more XIC peak groups is generally a subset of the spectral library or known compound database. This is because not all known compounds may be present in the sample. This number, however, can be large (>1,000) for complex samples, such as proteomic samples.

The measured retention times of the XIC peak groups of a subset of known compounds from the spectral library or known compound database serves as the dependent variables of the regression analysis. The known or theoretical retention times of the subset of known compounds from the spectral library or known compound database serve as the independent variables of the regression analysis. Using these independent and dependent variables, a regression function is calculated.

The known compounds of the sample are then identified in a second pass through the extracted data. In this second pass through the data, the known or theoretical retention times of the subset of known compounds are corrected using the calculated regression function. The corrected retention times are then compared to the measured retention times of the XIC peak groups of the subset of known compounds. The XIC peak groups that do not have measured retention times that correspond to the corrected retention times are removed. As a result, the remaining XIC peak groups of the subset of known compounds identify the known compounds present in the sample.

This regression analysis approach is possible because of the large amount data present in each DIA experiment. DIA methods provide a larger amount of data than targeted acquisition methods like SRM, for example. However, unlike targeted acquisition methods like SRM, DIA methods do not provide information about the specific precursor ions from which each product ion is produced.

Figure 2:
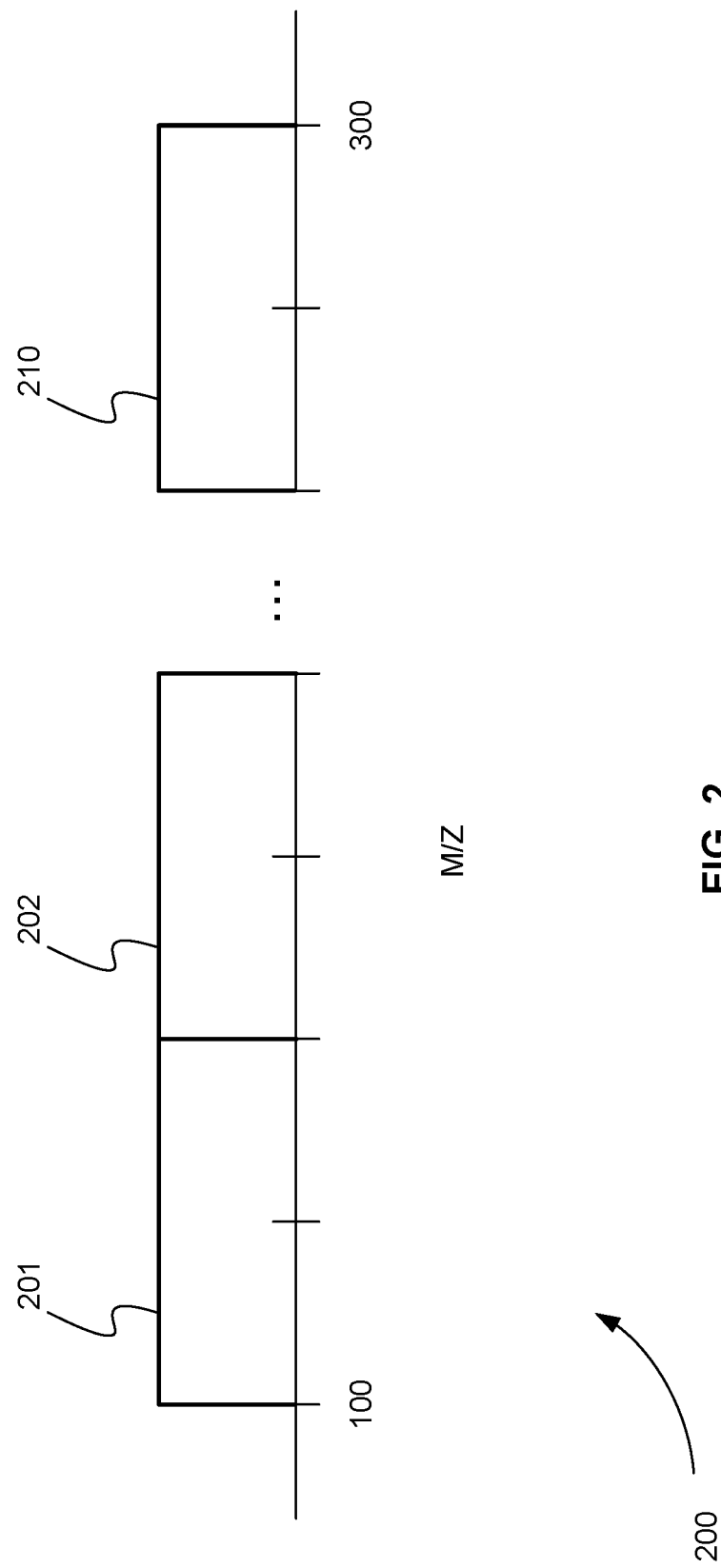
FIG. 2 is an exemplary diagram of a precursor ion mass-to-charge ratio (m/z) range that is divided into ten precursor ion mass selection windows for a data independent acquisition (DIA) workflow, in accordance with various embodiments.

FIG. 2 is an exemplary diagram 200 of a precursor ion mass-to-charge ratio (m/z) range that is divided into ten precursor ion mass selection windows for a data independent acquisition (DIA) workflow, in accordance with various embodiments. The m/z range shown in FIG. 2 is 200 m/z. Note that the terms "mass" and "m/z" are used interchangeably herein. Generally, mass spectrometry measurements are made in m/z and converted to mass by multiplying charge.

Each of the ten precursor ion mass selection or isolation windows spans or has a width of 20 m/z. Three of the ten precursor ion mass selection windows, windows 201, 202, and 210, are shown in FIG. 2. Precursor ion mass selection windows 201, 202, and 210 are shown as non-overlapping windows with the same width. In various embodiments, precursor ion mass selection windows can overlap and/or can have variable widths. U.S. patent application Ser. No. 14/401,032 describes using overlapping precursor ion mass selection windows in a single cycle of SWATH acquisition, for example. U.S. Pat. No. 8,809,772 describes using precursor ion mass selection windows with variable widths in a single cycle of SWATH acquisition using variable precursor ion mass selection windows in SWATH acquisition, for example. In a conventional SWATH acquisition, each of the ten precursor ion mass selection windows is selected and then fragmented, producing ten product ion spectra for the entire m/z range shown in FIG. 2.

FIG. 2 depicts non-variable and non-overlapping precursor ion mass selection windows used in a single cycle of an exemplary SWATH acquisition. A tandem mass spectrometer that can perform a SWATH acquisition method can further be coupled with a sample introduction device. In proteomics, for example, the proteins of a sample are typically digested using an enzyme, such as trypsin before the sample is introduced into the tandem mass spectrometer. As a result, the sample introduction device separates one or more proteins digested proteins, or peptides, from the sample over time, for example. A sample introduction device can introduce a sample to the tandem mass spectrometer using a technique that includes, but is not limited to, injection, liquid chromatography, gas chromatography, capillary electrophoresis, or ion mobility. The separated one or more peptides are ionized by an ion source, producing an ion beam of precursor ions of the one or more proteins that are selected and fragmented by the tandem mass spectrometer.

As a result, for each time step of a sample introduction of separated proteins, each of the ten precursor ion mass selection windows is selected and then fragmented, producing ten product ion spectra for the entire m/z range. In other words, each of the ten precursor ion mass selection windows is selected and then fragmented during each cycle of a plurality of cycles.

Figure 3:
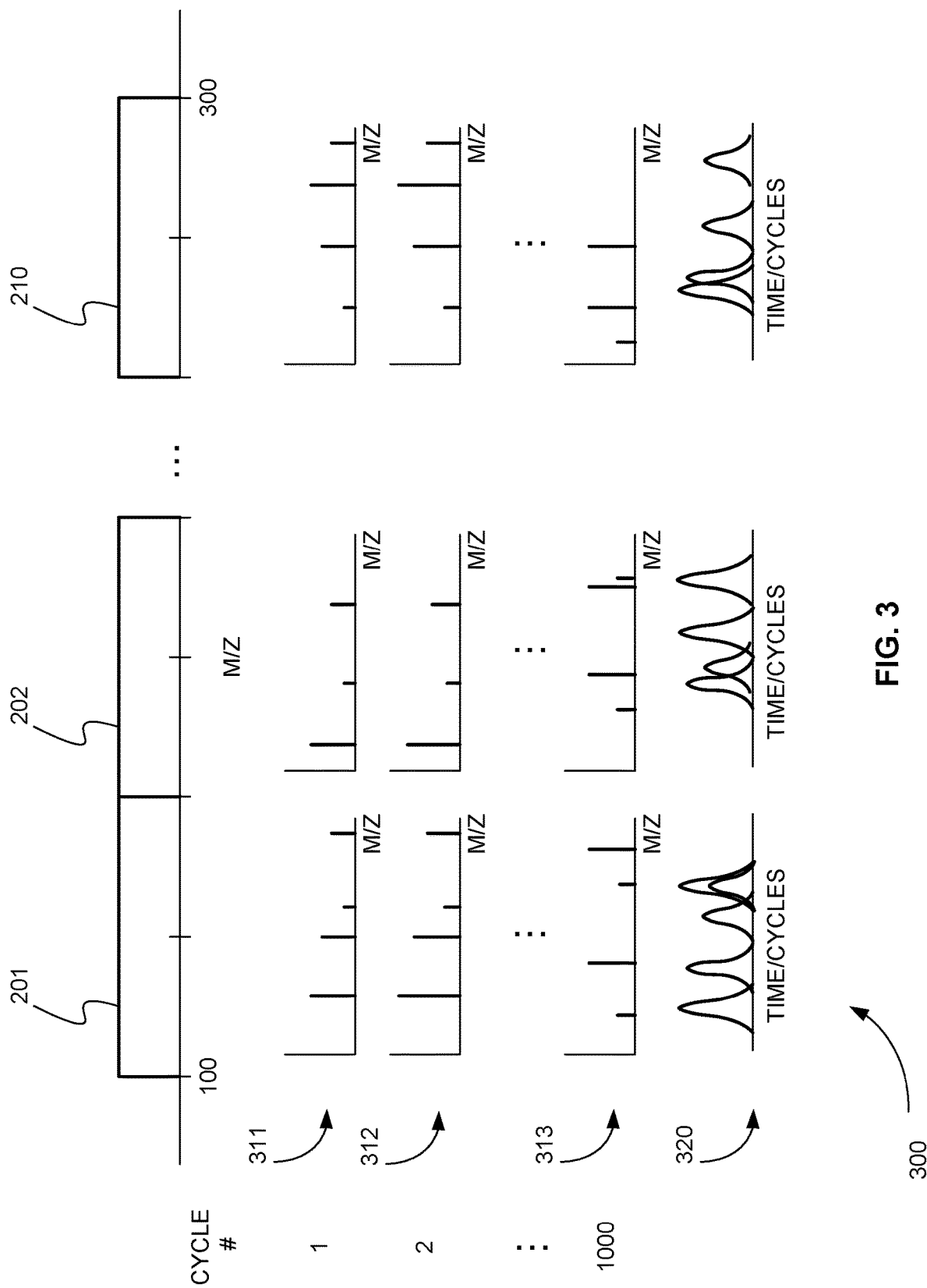
FIG. 3 is an exemplary diagram that graphically depicts the steps for obtaining product ion traces or XICs from each precursor ion mass selection window during each cycle of a DIA workflow, in accordance with various embodiments.

FIG. 3 is an exemplary diagram 300 that graphically depicts the steps for obtaining product ion traces or XICs from each precursor ion mass selection window during each cycle of a DIA workflow, in accordance with various embodiments. For example, ten precursor ion mass selection windows, represented by precursor ion mass selection windows 201, 202, and 210 in FIG. 3, are selected and fragmented during each cycle of a total of 1000 cycles.

During each cycle, a product ion spectrum is obtained for each precursor ion mass selection window. For example, product ion spectrum 311 is obtained by fragmenting precursor ion mass selection window 201 during cycle 1, product ion spectrum 312 is obtained by fragmenting precursor ion mass selection window 201 during cycle 2, and product ion spectrum 313 is obtained by fragmenting precursor ion mass selection window 201 during cycle 1000.

By plotting the intensities of the product ions in each product ion spectrum of each precursor ion mass selection window over time, XICs are obtained for each precursor ion mass selection window. For example, XIC 320 is calculated from the 1,000th product ion spectra of precursor ion mass selection window 201. XIC 320 includes XIC peaks or traces for all of the product ions that are produced from fragmenting precursor ion mass selection window 201 during the 1000 cycles. Note that XICs can be plotted in terms of time or cycles.

XIC 320 is shown plotted in two dimensions in FIG. 3. However, each XIC of each precursor ion mass selection window is actually three-dimensional, because the different XIC peaks represent different m/z values.

Figure 4:
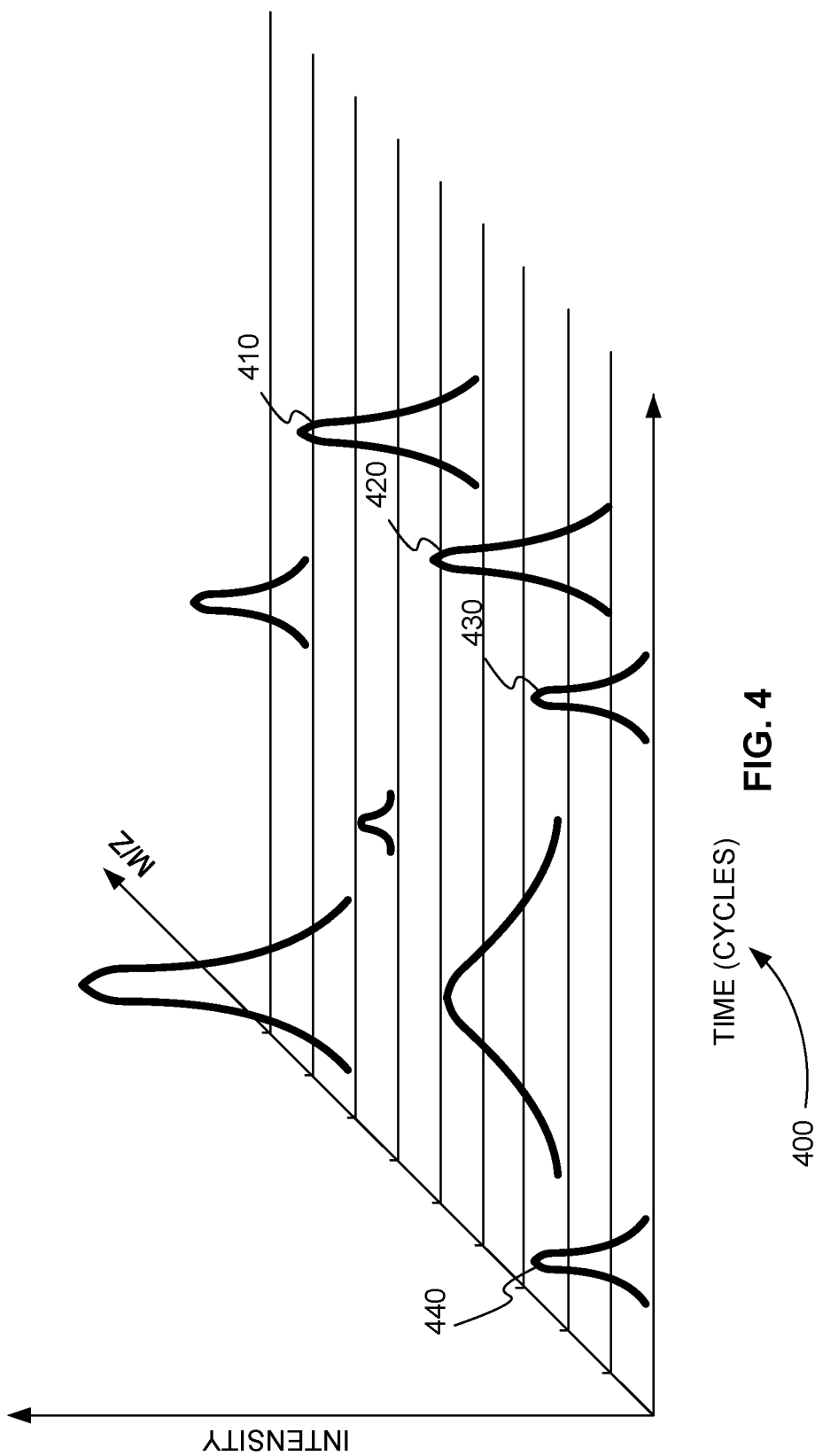
FIG. 4 is an exemplary diagram that shows the three-dimensionality of an XIC obtained for a precursor ion mass selection window over time, in accordance with various embodiments.

FIG. 4 is an exemplary diagram 400 that shows the three-dimensionality of an XIC obtained for a precursor ion mass selection window over time, in accordance with various embodiments. In FIG. 4, the x-axis is time or cycle number, the y-axis is product ion intensity, and the z-axis is m/z. From this three-dimensional plot, more information is obtained.

For example, XIC peaks 410 and 420 both have the same shape and occur at the same time, or same retention time. However, XIC peaks 410 and 420 have different m/z values. This may mean that XIC peaks 410 and 420 are isotopic peaks or represent different product ions from the same precursor ion. If XIC peaks 410 and 420 represent different product ions from the same precursor ion, they can be grouped into an XIC peak group, for example. An XIC peak group is a group of one or more XIC peaks that have the same retention time.

Similarly, XIC peaks 430 and 440 have the same m/z value but occur at different times. This may mean that XIC peaks 430 and 440 are the same product ion, but they are from two different precursor ions. XIC peaks 430 and 440 show that an accurate retention time is needed to determine the correct product ion XIC peak for each known compound.

After obtaining product ion experimental data using a DIA method, known compounds in a sample are identified by comparing known product ions of a spectral library or theoretical product ions generated from a known compound database to the product ion experimental data. A spectral library includes one or more spectra previously obtained for each known compound in the library. The spectra were obtained for samples that included only one known compound, for example. Theoretical product ions are computationally generated from stored information about the one or more known compounds. This stored information can be stored in many different forms including, but not limited to, databases and flat files.

In various embodiments, stored information about known proteins or peptides is obtained from a FASTA file. The FASTA file is parsed. The proteins parsed from the FASTA file are then computationally digested using the same enzyme used to digest the sample in the experiments. Computational digestion of the one or more known proteins produces one or more theoretical peptides, or one or more peptide precursor ions, for each protein. Theoretical product ions for each protein are obtained by computationally fragmenting theoretical peptide precursor ions of each protein. For example, theoretical product ions are obtained by selecting the b and y fragments of theoretical peptide precursor ions.

As described above, retention time is particularly helpful in identifying known compounds in a DIA experiment, because the product ions in each mass spectrum may be from more than one precursor ion. As a result, it is important that the retention times used to identify known compounds are as accurate as possible. Also, as described above, the retention times obtained from spectral libraries or calculated for theoretical product ions do not correspond to retention times measured in a sample due to a difference in sample media used for the spectral library or to a difference in separation that was theoretically calculated.

In various embodiments, the retention times obtained from spectral libraries or calculated for theoretical product ions are corrected using regression analysis. As described above, in a first pass through the data, the measured product ion data is extracted without regard to retention time. The extracted measured product ion data includes an XIC for each product ion of a spectral library or each theoretical product ion generated for a known compound database. XIC peaks above a predetermined intensity threshold value are found in the extracted XICs. The XIC peaks found are then grouped by their measured retention times.

The measured retention times of the XIC peak groups of a subset of known compounds from the spectral library or known compound database serves as the dependent variables of the regression analysis. The known or theoretical retention times of the subset of known compounds from the spectral library or known compound database serve as the independent variables of the regression analysis.

Figure 5:
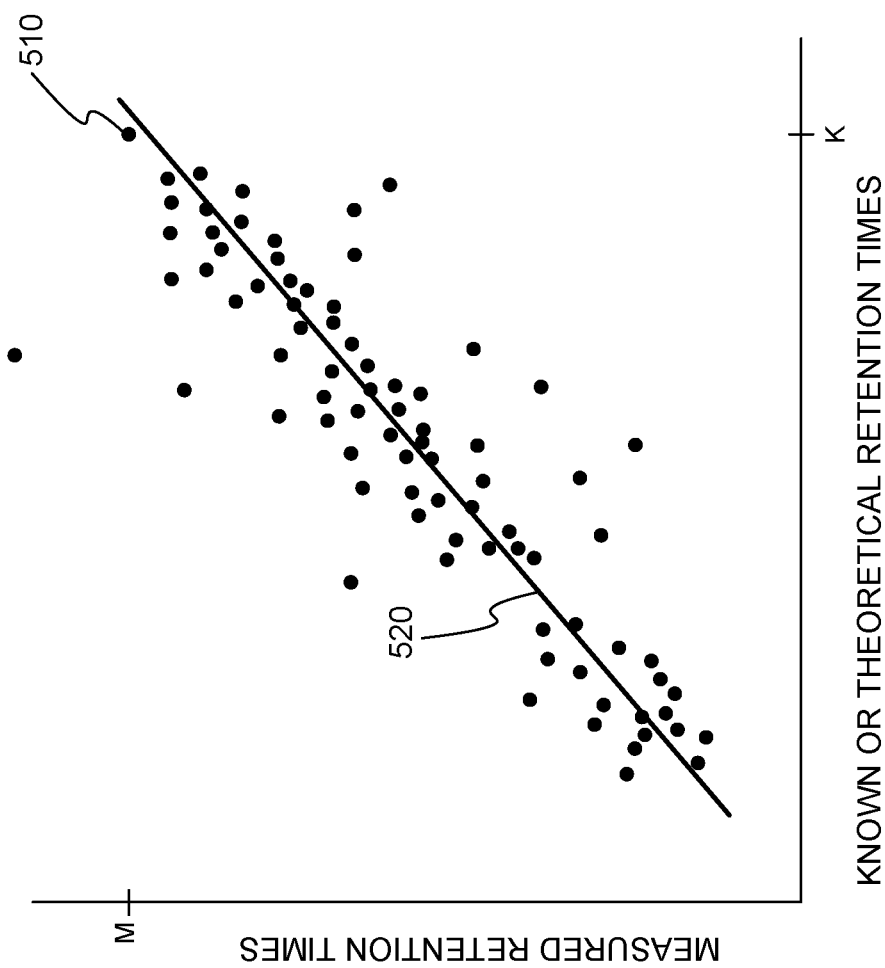
FIG. 5 is an exemplary plot showing a subset of known compounds of a spectral library or database of known compounds that have XIC peak groups in a sample plotted with respect to the measured retention times of their XIC peak groups and their known or theoretical retention times, in accordance with various embodiments.

FIG. 5 is an exemplary plot 500 showing a subset of known compounds of a spectral library or database of known compounds that have XIC peak groups in a sample plotted with respect to the measured retention times of their XIC peak groups and their known or theoretical retention times, in accordance with various embodiments. Known compound 510, for example, is from a spectral library or database of known compounds and is found to have a peak group in the sample with an intensity that is greater than a predetermined intensity threshold value. Since not all known compounds in spectral library or database of known compounds have a peak group in the sample with an intensity that is greater than a predetermined intensity threshold value, known compound 510 is part of a subset of the spectral library or database of known compounds.

Known compound 510 is positioned at the intersection of its known or theoretical retention time, K, and the measured retention time of its peak group in the sample, M. By also obtaining a plurality of other known compounds that have at least one peak group in the sample with an intensity greater than the predetermined intensity threshold value, regression analysis can be performed on this data to determine how the measured retention time of a peak group of a known compound varies in the sample with respect to the known or theoretical retention of the known compound.

If linear regression analysis is performed, a linear function is found from the data. This linear function is represented by line 520, for example, in FIG. 5. Various embodiments, however, are not limited to linear regression analysis. Any form of regression analysis can be performed including, but not limited to, linear or nonlinear regression analysis.

In various embodiments also, not all known compounds that have at least one peak group in the sample with an intensity greater than the predetermined intensity threshold value may be used in the regression analysis. For example, known compounds known to have modified forms or known to produce mis-cleavages may be excluded.

System for Correcting Retention Times

Figure 6:
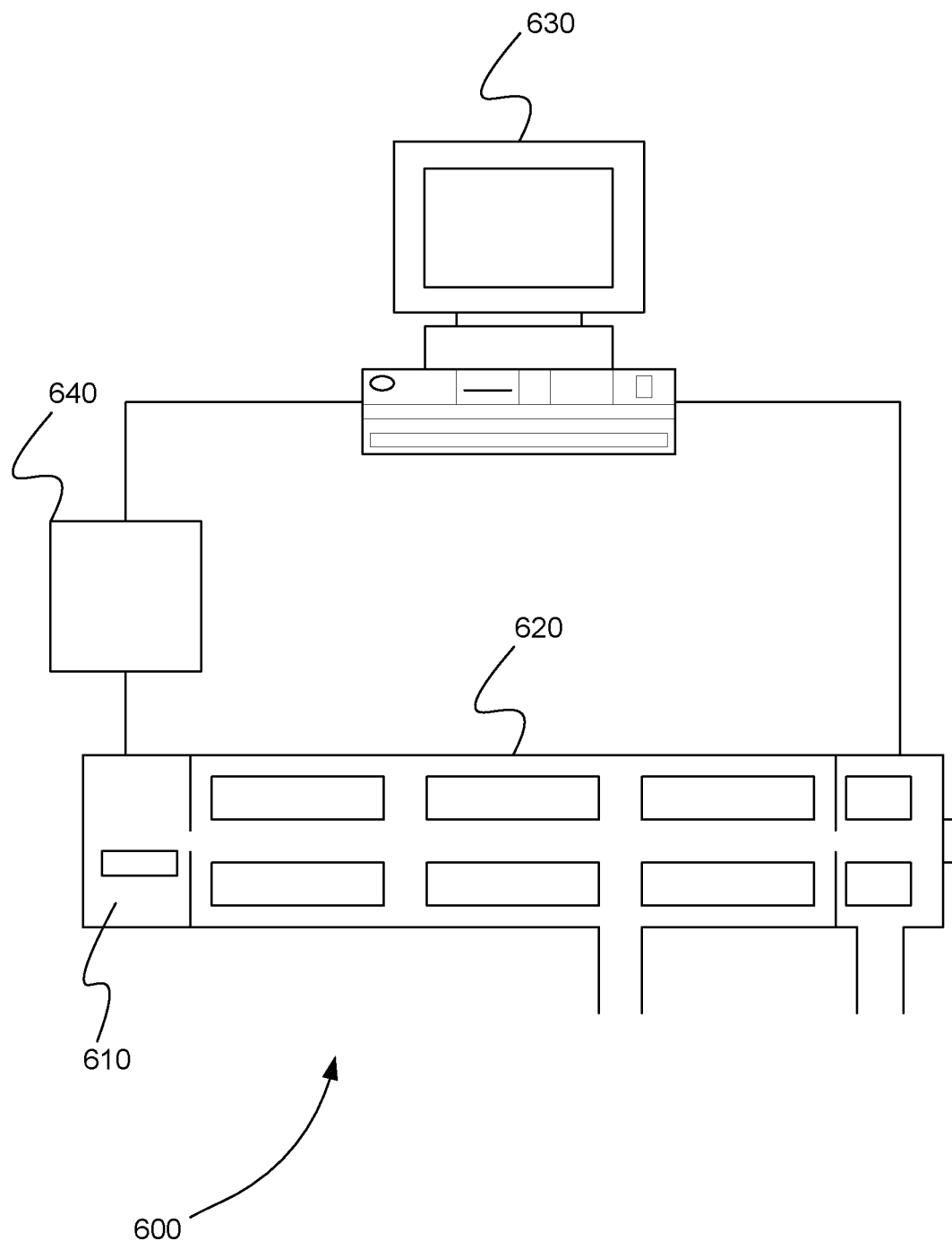
FIG. 6 is a schematic diagram of a system for automatically calculating a regression function to describe how the known retention times of a spectral library of known compounds are varied by the sample in a tandem mass spectrometry DIA experiment, in accordance with various embodiments.

FIG. 6 is a schematic diagram of a system 600 for automatically calculating a regression function to describe how the known retention times of a spectral library of known compounds are varied by the sample in a tandem mass spectrometry DIA experiment, in accordance with various embodiments. System 600 includes ion source 610, tandem mass spectrometer 620, and processor 630. In various embodiments, system 600 can also include separation device 640.

Separation device 640 can separate compounds from a sample over time using one of a variety of techniques. These techniques include, but are not limited to, ion mobility, gas chromatography (GC), liquid chromatography (LC), capillary electrophoresis (CE), or flow injection analysis (FIA).

Ion source 610 can be part of tandem mass spectrometer 620, or can be a separate device. Ion source 610 receives the plurality of compounds from separation device 640 and ionizes the plurality of compounds, producing an ion beam of precursor ions.

Tandem mass spectrometer 620 can include, for example, one or more physical mass filters and one or more physical mass analyzers. A mass analyzer of tandem mass spectrometer 620 can include, but is not limited to, a time-of-flight (TOF), quadrupole, an ion trap, a linear ion trap, an orbitrap, or a Fourier transform mass analyzer.

Tandem mass spectrometer 620 receives the ion beam from ion source 610. Tandem mass spectrometer 620 divides an m/z range of the ion beam into two or more precursor ion mass selection windows and selects and fragments the two or more precursor ion mass selection windows during each cycle of a plurality of cycles, producing a plurality of measured product ion spectra.

Processor 630 can be, but is not limited to, a computer, microprocessor, or any device capable of sending and receiving control signals and data from tandem mass spectrometer 620 and processing data. Processor 630 can be, for example, computer system 100 of FIG. 1. In various embodiments, processor 630 is in communication with tandem mass spectrometer 620 and separation device 640.

Processor 630 performs a number of steps. In step (a), processor 630 receives the plurality of measured product ion spectra from tandem mass spectrometer 620. In step (b), processor 630 retrieves from a spectral library of known compounds one or more product ions for each known compound. Alternatively, in various embodiments, processor 630 retrieves a plurality of known compounds from a database. For example, the database can be a protein or peptide database. For each known compound of the database, processor 630 theoretically fragments the known compound, producing one or more theoretical product ions.

In step (c), for each product ion of each known compound of the spectral library or the database, processor 630 calculates an XIC from the plurality of measured product ion spectra. In step (d), processor 630 groups XIC peaks with an intensity above a predetermined intensity threshold value from the XICs calculated for each known compound of the spectral library by the measured retention time. One or more measured XIC peak groups are produced for a subset of known compounds of the spectral library that have measured XIC peaks with an intensity above the predetermined intensity threshold value.

In step (e), processor 630 retrieves from the spectral library a known retention time for each known compound of the subset of known compounds. Alternatively, for known compounds obtained from a database, processor 630 calculates a theoretical retention time for each known compound of the subset of known compounds.

Finally, in step (f), processor 630 calculates a regression function to describe how the known retention times of the spectral library or the theoretical retention times calculated for the known compound database are varied in the sample. The regression function is calculated using the known or theoretical retention times of the subset of known compounds as the independent variables. The measured retention times of the measured XIC peak groups of the subset of known compounds are used as the dependent variables.

In various embodiments, only one measured XIC peak group of each known compound of the subset of known compounds is used in calculating the regression function.

In various embodiments, before step (e), processor 630 removes from the subset of known compounds any measured XIC peak group that represents modifications or mis-cleavages of a known compound.

In various embodiments, the regression function calculated in step (f) is a linear regression function or a nonlinear regression function.

In various embodiments, processor 630 further identifies known compounds in the sample. In step (g), processor 630 calculates a corrected retention time for each known compound of the subset of known compounds using the regression function and the known or theoretical retention time for each known compound.

In step (h), processor 630 compares a corrected retention time for each known compound of the subset of known compounds with a measured retention time of each measured XIC peak group of each known compound. Processor 630 removes the measured XIC peak group if the measured retention time of the measured XIC peak group is not within a predetermined retention time threshold value of the corrected retention time of each known compound. The predetermined retention time threshold value essentially establishes a confidence interval around the regression line of the data. Those XIC peak groups that fall within the confidence interval are taken as the correct XIC peak groups.

Finally, in step (i) processor 630 identifies known compounds of the sample as the known compounds of the subset of known compounds that have a remaining measured XIC peak group.

Method for Correcting Retention Times of a Spectral Library

Figure 7:
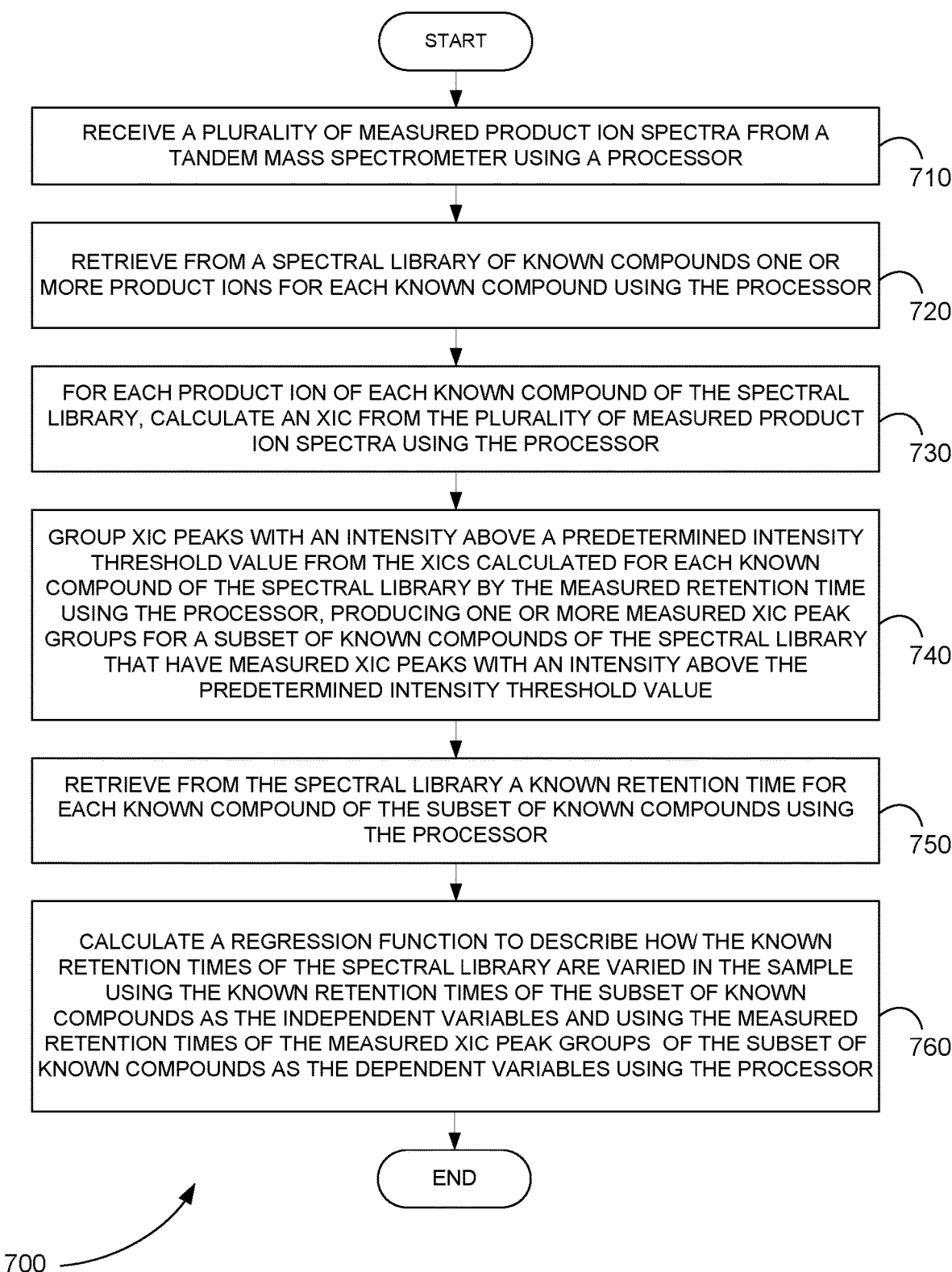
FIG. 7 is a flowchart showing a method for automatically calculating a regression function to describe how the known retention times of a spectral library of known compounds are varied by the sample in a tandem mass spectrometry DIA experiment, in accordance with various embodiments.

FIG. 7 is a flowchart showing a method 700 for automatically calculating a regression function to describe how the known retention times of a spectral library of known compounds are varied by the sample in a tandem mass spectrometry DIA experiment, in accordance with various embodiments.

In step 710 of method 700, a plurality of measured product ion spectra are received from a tandem mass spectrometer using a processor. The plurality of measured product ion spectra is produced by the tandem mass spectrometer by dividing an m/z range of an ion beam into two or more precursor ion mass selection windows and selecting and fragmenting the two or more precursor ion mass selection windows during each cycle of a plurality of cycles. The ion beam is produced by an ion source that ionizes a plurality of compounds, producing an ion beam of precursor ions. The plurality of compounds is separated from a sample by a separation device.

In step 720, one or more product ions for each known compound are retrieved from a spectral library of known compounds using the processor.

In step 730, for each product ion of each known compound of the spectral library, an XIC is calculated from the plurality of measured product ion spectra using the processor.

In step 740, XIC peaks with an intensity above a predetermined intensity threshold value from the XICs calculated for each known compound of the spectral library are grouped by the measured retention time using the processor, producing one or more measured XIC peak groups for a subset of known compounds of the spectral library that have measured XIC peaks with an intensity above the predetermined intensity threshold value.

In step 750, a known retention time for each known compound of the subset of known compounds is retrieved from the spectral library using the processor.

In step 760, a regression function is calculated to describe how the known retention times of the spectral library are varied in the sample using the processor. The known retention times of the subset of known compounds are used as the independent variables. The measured retention times of the measured XIC peak groups of the subset of known compounds are used as the dependent variables.

Method for Correcting Theoretical Retention Times

Figure 8:
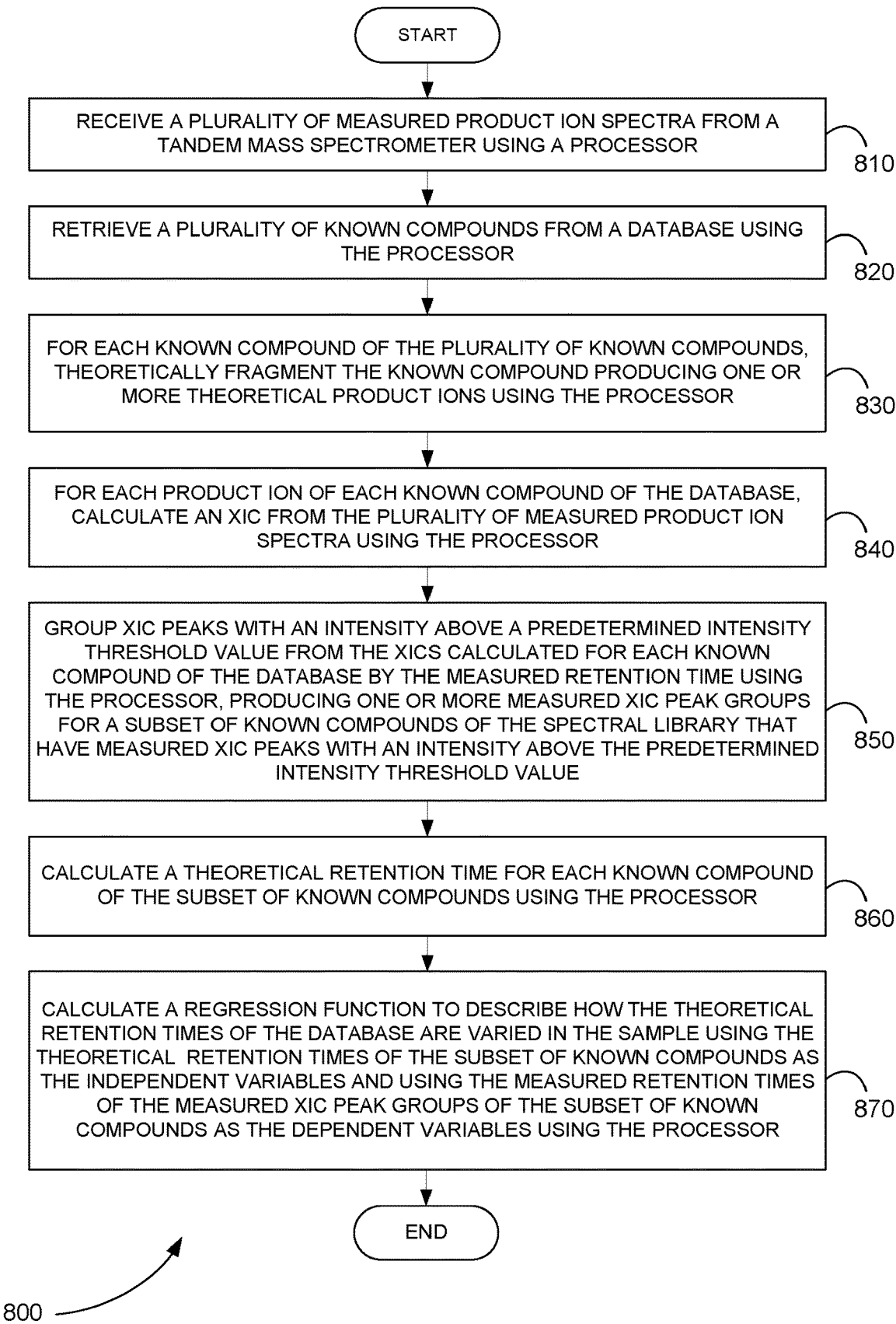
FIG. 8 is a flowchart showing a method for automatically calculating a regression function to describe how the theoretical retention times of the theoretical product ions of known compounds are varied by the sample in a tandem mass spectrometry DIA experiment, in accordance with various embodiments.

FIG. 8 is a flowchart showing a method 800 for automatically calculating a regression function to describe how the theoretical retention times of the theoretical product ions of known compounds are varied by the sample in a tandem mass spectrometry DIA experiment, in accordance with various embodiments.

In step 810 of method 800, a plurality of measured product ion spectra is received from a tandem mass spectrometer using a processor. The plurality of measured product ion spectra is produced by the tandem mass spectrometer by dividing an m/z range of an ion beam into two or more precursor ion mass selection windows and selecting and fragmenting the two or more precursor ion mass selection windows during each cycle of a plurality of cycles. The ion beam is produced by an ion source that ionizes a plurality of compounds, producing an ion beam of precursor ions. The plurality of compounds is separated from a sample by a separation device.

In step 820, a plurality of known compounds is retrieved from a database using the processor.

In step 830, for each known compound of the plurality of known compounds, the known compound is theoretically fragmented producing one or more theoretical product ions using the processor.

In step 840, for each product ion of each known compound of the database, an XIC is calculated from the plurality of measured product ion spectra using the processor.

In step 850, XIC peaks with an intensity above a predetermined intensity threshold value from the XICs calculated for each known compound of the database are grouped by the measured retention time using the processor, producing one or more measured XIC peak groups for a subset of known compounds of the spectral library that have measured XIC peaks with an intensity above the predetermined intensity threshold value.

In step 860, a theoretical retention time is calculated for each known compound of the subset of known compounds using the processor.

In step 870, a regression function is calculated to describe how the theoretical retention times of the database are varied in the sample using the processor. The theoretical retention times of the subset of known compounds are used as the independent variables. The measured retention times of the measured XIC peak groups of the subset of known compounds are used as the dependent variables.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for automatically calculating a regression function to describe how the known retention times of a spectral library of known compounds are varied by the sample in a tandem mass spectrometry data independent acquisition (DIA) experiment, comprising:
   a separation device that separates a plurality of compounds from a sample over time;
   an ion source that receives the plurality of compounds from the separation device and ionizes the plurality of compounds, producing an ion beam of precursor ions;
   a tandem mass spectrometer that receives the ion beam, divides a mass-to-charge ratio (m/z) range of the ion beam into two or more precursor ion mass selection windows, and selects and fragments the two or more precursor ion mass selection windows during each cycle of a plurality of cycles, producing a plurality of measured product ion spectra; and
   a processor in communication with the tandem mass spectrometer that
   (a) receives the plurality of measured product ion spectra from the tandem mass spectrometer,
   (b) retrieves from a spectral library of known compounds one or more product ions for each known compound,
   (c) for each product ion of each known compound of the spectral library, calculates an extracted ion chromatogram (XIC) from the plurality of measured product ion spectra,
   (d) groups XIC peaks with an intensity above a predetermined intensity threshold value from the XICs calculated for each known compound of the spectral library by the measured retention time, producing one or more measured XIC peak groups for a subset of known compounds of the spectral library that have measured XIC peaks with an intensity above the predetermined intensity threshold value, (e) retrieves from the spectral library a known retention time for each known compound of the subset of known compounds, and (f) calculates a regression function to describe how the known retention times of the spectral library are varied in the sample using the known retention times of the subset of known compounds as the independent variables and using the measured retention times of the measured XIC peak groups of the subset of known compounds as the dependent variables.

2. The system of claim 1, wherein the processor further, before step (e), removes from the subset of known compounds any measured XIC peak group that represents modifications or mis-cleavages of a known compound.

3. The system of claim 1, wherein the regression function of step (f) comprises a linear regression function.

4. The system of claim 1, wherein the regression function of step (f) comprises a nonlinear regression function.

5. The system of claim 1, wherein the processor further identifies known compounds in the sample by (g) calculating a corrected retention time for each known compound of the subset of known compounds using the regression function and the known retention time for the each known compound, (h) comparing a corrected retention time for each known compound of the subset of known compounds with a measured retention time of each measured XIC peak group of the each known compound and removing the each measured XIC peak group if the measured retention time of the each measured XIC peak group is not within a predetermined retention time threshold value of the corrected retention time of the each known compound, and (i) identifying known compounds of the sample as known compounds of the subset of known compounds that have a remaining measured XIC peak group.

6. A system for automatically calculating a regression function to describe how the theoretical retention times of the theoretical product ions of known compounds are varied by the sample in a tandem mass spectrometry data independent acquisition (DIA) experiment, comprising:

a separation device that separates a plurality of compounds from a sample over time;

an ion source that receives the plurality of compounds from the separation device and ionizes the plurality of compounds, producing an ion beam of precursor ions;

a tandem mass spectrometer that receives the ion beam, divides a mass-to-charge ratio (m/z) range of the ion beam into two or more precursor ion mass selection windows, and selects and fragments the two or more precursor ion mass selection windows during each cycle of a plurality of cycles, producing a plurality of measured product ion spectra; and a processor in communication with the tandem mass spectrometer that (a) receives the plurality of measured product ion spectra from the tandem mass spectrometer, (b) retrieves a plurality of known compounds from a database, (c) for each known compound of the plurality of known compounds, theoretically fragments the known compound producing one or more theoretical product ions, (d) for each product ion of each known compound of the database, calculates an extracted ion chromatogram (XIC) from the plurality of measured product ion spectra, (e) groups XIC peaks with an intensity above a predetermined intensity threshold value from the XICs calculated for each known compound of the database by the measured retention time, producing one or more measured XIC peak groups for a subset of known compounds of the database that have measured XIC peaks with an intensity above the predetermined intensity threshold value, (f) calculates a theoretical retention time for each known compound of the subset of known compounds, and (g) calculates a regression function to describe how the known retention times of the database are varied in the sample using the theoretical retention times of the subset of known compounds as the independent variables and using the measured retention times of the measured XIC peak groups of the subset of known compounds as the dependent variables.

7. The system of claim 6, wherein the processor further, before step (f), removes from the subset of known compounds any measured XIC peak group that represents modifications or mis-cleavages of a known compound.

8. The system of claim 6, wherein the regression function of step (g) comprises a linear regression function.

9. The system of claim 6, wherein the regression function of step (g) comprises a nonlinear regression function.

10. The system of claim 6, wherein the processor further identifies known compounds in the sample by (h) calculating a corrected retention time for each known compound of the subset of known compounds using the regression function and the theoretical retention time for the each known compound, (i) comparing a corrected retention time for each known compound of the subset of known compounds with a measured retention time of each measured XIC peak group of the each known compound and removing the each measured XIC peak group if the measured retention time of the each measured XIC peak group is not within a predetermined retention time threshold value of the corrected retention time of the each known compound, and (j) identifying known compounds of the sample as known compounds of the subset of known compounds that have a remaining measured XIC peak group.

11. A method for automatically calculating a regression function to describe how the known retention times of a spectral library of known compounds are varied by the sample in a tandem mass spectrometry data independent acquisition (DIA) experiment, comprising:

(a) receiving a plurality of measured product ion spectra from a tandem mass spectrometer using a processor,
wherein the plurality of measured product ion spectra are produced by the tandem mass spectrometer by dividing a mass-to-charge ratio (m/z) range of an ion beam into two or more precursor ion mass selection windows and selecting and fragmenting the two or more precursor ion mass selection windows during each cycle of a plurality of cycles,
wherein the ion beam is produced by an ion source that ionizes a plurality of compounds, producing an ion beam of precursor ions, and
wherein the plurality of compounds is separated from a sample by a separation device;

(b) retrieving from a spectral library of known compounds one or more product ions for each known compound using the processor;

(c) for each product ion of each known compound of the spectral library, calculating an extracted ion chromatogram (XIC) from the plurality of measured product ion spectra using the processor;

(d) grouping XIC peaks with an intensity above a predetermined intensity threshold value from the XICs calculated for each known compound of the spectral library by the measured retention time using the processor, producing one or more measured XIC peak groups for a subset of known compounds of the spectral library that have measured XIC peaks with an intensity above the predetermined intensity threshold value;

(e) retrieving from the spectral library a known retention time for each known compound of the subset of known compounds using the processor; and (f) calculating a regression function to describe how the known retention times of the spectral library are varied in the sample using the known retention times of the subset of known compounds as the independent variables and using the measured retention times of the measured XIC peak groups of the subset of known compounds as the dependent variables using the processor.

12. The method of claim 11, further comprising, before step (e), removing from the subset of known compounds any measured XIC peak group that represents modifications or mis-cleavages of a known compound.

13. The method of claim 11, wherein the regression function of step (f) comprises a linear regression function or a nonlinear regression function.

14. The method of claim 11, further comprising (g) calculating a corrected retention time for each known compound of the subset of known compounds using the regression function and the known retention time for the each known compound using the processor, (h) comparing a corrected retention time for each known compound of the subset of known compounds with a measured retention time of each measured XIC peak group of the each known compound and removing the each measured XIC peak group if the measured retention time of the each measured XIC peak group is not within a predetermined retention time threshold value of the corrected retention time of the each known compound using the processor, and (i) identifying known compounds of the sample as known compounds of the subset of known compounds that have a remaining measured XIC peak group using the processor.

* * * * *